US00PP31184P2

(12) United States Plant Patent
Heuger

(10) Patent No.: US PP31,184 P2
(45) Date of Patent: Dec. 3, 2019

(54) ***HELLEBORUS* PLANT NAMED 'COSEH 5000'**

(50) Latin Name: ***Helleborus* x *ericsmithii* X *Helleborus* x *hybridus***
Varietal Denomination: COSEH 5000

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/350,425

(22) Filed: Nov. 15, 2018

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 6/72
See application file for complete search history.

(56) References Cited

PUBLICATIONS

PLUTO Plant Variety Database Jun. 4, 2019. p. 1.*

* cited by examiner

*Primary Examiner* — Annette H Para
(74) *Attorney, Agent, or Firm* — C. A. Whealy

(57) ABSTRACT

A new and distinct cultivar of *Helleborus* plant named 'COSEH 5000', characterized by its upright and mounded plant habit; moderately vigorous growth habit; dark green-colored leaves; moderately freely flowering habit; single white and greyed purple bi-colored flowers; and good garden performance.

2 Drawing Sheets

Botanical designation: *Helleborus* x *ericsmithii* X *Helleborus* x *hybridus*.
Cultivar denomination: 'COSEH 5000'.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 5000'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2014.

Asexual reproduction of the new *Helleborus* plant by divisions in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5000'. These characteristics in combination distinguish 'COSEH 5000' as a new and distinct *Helleborus* plant:

1. Upright and mounded plant habit.
2. Moderately vigorous growth habit.
3. Dark green-colored leaves.
4. Moderately freely flowering habit.
5. Single white and greyed purple bi-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have white and greyed purple bi-colored flowers whereas plants of the female parent selection have cream-colored flowers.

Plants of the new *Helleborus* differ from plants of the male parent selection in the following characteristics:

1. Plants of the new *Helleborus* are taller than plants of the male parent selection.
2. Plants of the new *Helleborus* have darker green-colored leaves than plants of the male parent selection.

Plants of the new *Helleborus* can be compared to plants of *Helleborus* x *hybridus* 'Annas Red', not patented. In side-by-side comparisons, plants of the new *Helleborus* differ primarily from plants of 'Annas Red' in the following characteristics:

1. Plants of the new *Helleborus* have less distinct leaf venation than plants of 'Annas Red'.

2. Plants of the new *Helleborus* flower earlier than plants of 'Annas Red'.
3. Flowers of plants of the new *Helleborus* are white and greyed purple bi-colored whereas flowers of plants of 'Armas Red' are red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 5000' grown in a container.

The photograph on the second sheet is a close-up view of typical flowers of 'COSEH 5000'.

DETAILED BOTANICAL DESCRIPTION

The aforementioned photographs and following observations, measurements and values describe plants grown during November in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 16 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 5000'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous growth habit; moderate growth rate.

*Plant height, soil level to top of foliar plane*.—About 21.2 cm.

*Plant height, soil level to top of flowers*.—About 31.8 cm.

*Plant diameter* (*area of spread*).—About 44 cm.

Leaf description:

*Arrangement*.—Leaves arranged in a basal rosette; leaves palmately compound with typically five leaflets per leaf.

*Leaf length*.—About 21.7 cm.

*Leaf width*.—About 23.7 cm.

*Leaflet length*.—About 13.1 cm.

*Leaflet width*.—About 6.5 cm.

*Leaf shape*.—Palmate; reniform in outline.

*Leaflet shape*.—Obovate to elliptic, occasionally ovate.

*Leaflet apex*.—Acute.

*Leaflet base*.—Attenuate.

*Leaflet margin*.—Coarsely serrate; moderately undulate.

*Leaflet texture and luster, upper surface*.—Smooth, glabrous; leathery; glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137C; towards the base, tinged with close to 187C. Developing leaflets, lower surface: Close to 148A; venation, close to 187A to 187B. Fully developed leaflets, upper surface: Close to darker than between NN137A and 147A; venation, close to 138B. Fully developed leaflets, lower surface: Close to 147B; venation, close to 166A.

*Petioles*.—Length: About 14.1 cm. Diameter: About 6 mm to 7 mm. Strength: Strong. Texture and luster, upper and lower surfaces: Smooth, glabrous; moderately glossy. Color, upper and lower surfaces: Close to 144A to 144B; densely covered with small dots, close to N199A.

Flower description:

*Flower shape and habit*.—Single rotate flowers; arranged solitary or in clusters with about 19 flowers each; moderately freely flowering habit with about 33 flowers developing per plant; flowers facing outwardly to moderately nodding.

*Fragrance*.—None detected.

*Natural flowering season*.—Plants begin flowering about ten months after planting; plants flower during the late autumn into the winter in Germany.

*Flower longevity on the plant*.—About ten days; sepals persistent, other flower parts are not persistent.

*Flower buds*.—Length: About 2.6 cm. Diameter: About 1.7 cm. Shape: Oblong to broadly ovoid. Texture and luster: Smooth, glabrous; matte. Color: Close to 155A flushed with close to 145C to 145D; towards the apex and margins, close to 63B.

*Inflorescence height*.—About 32.3 cm.

*Inflorescence diameter*.—About 22.8 cm.

*Flower diameter*.—About 7.6 cm.

*Flower depth* (*height*).—About 2.7 cm.

*Petals*.—Transformed into nectaries.

*Sepals*.—Quantity and arrangement: About five, arranged in a single whorl. Length: About 4.7 cm. Width: About 4.5 cm. Shape: Broadly rhomboidal, moderately concave. Apex: Obtuse. Base: Cuneate. Margin: Entire; moderately undulate. Texture and luster, upper surface: Smooth, glabrous; matte. Texture and luster, lower surface: Smooth, glabrous; slightly glossy. Color: When opening, upper surface: Close to NN155C; towards the margins with close to 184D. When opening, lower surface: Close to NN155C; towards the margins, close to 186A; venation, close to 186A. Fully opened, upper surface: Close to N155B and 157B flushed with close to 186A; towards the margins, close to 186A. Fully opened, lower surface: Close to N155B; towards the margins, close to 186A; venation, close to 186A.

*Flower bracts*.—Quantity per flower: Typically two. Length: About 7.2 cm. Width: About 4.8 cm. Shape: Broadly ovate. Apex: Acute. Base: Truncate. Margin: Serrate; moderately undulate. Color, upper surface: Close to NN137B. Color, lower surface: Close to 147B; venation, close to 187A.

*Peduncles*.—Length: About 27.2 cm. Diameter: About 0.8 cm to 1.2 cm. Aspect: About 10° from vertical. Strength: Strong. Texture and luster: Smooth, glabrous; moderately glossy. Color: Close to 146D; fine dots, close to 178A to 178B.

*Pedicels*.—Length: About 5.1 cm. Diameter: About 3 mm. Aspect: About 30° from peduncle axis. Strength: Moderately strong. Texture and luster: Smooth, glabrous; moderately glossy. Color: Close to 194C; fine dots, close to 183D.

*Reproductive organs*.—Stamens: Quantity per flower: About 100. Filament length: About 1.9 cm. Filament color: Close to NN155D. Anther shape: Reniform; basifixed. Anther size: About 2 mm by 3 mm. Anther color: Close to 154C to 154D. Pollen amount: Moderate. Pollen color: Close to 4D. Pistils: Quantity per flower: About four to six. Pistil length: About 1.4 cm. Stigma diameter: About 0.3 mm. Stigma shape: Club-shaped. Stigma color: Close to 157D. Style length: About 1.35 cm. Style color: Close to 186B. Ovary color: Close to 145C. Nectaries (transformed petals): Quantity per flower: About 14. Length: About 1.2 cm. Diameter: About 4 mm. Shape: Tubular, flattened. Texture and luster, inner and outer surfaces:. Smooth, glabrous; slightly glossy. Color, immature, inner and outer surfaces: Close to 144C; distally, close to 150B. Color, mature, inner and outer surfaces: Close to N144A; distally, close to 151B; color becoming closer to 146C and distally, close to 12A, with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5000' as illustrated and described.

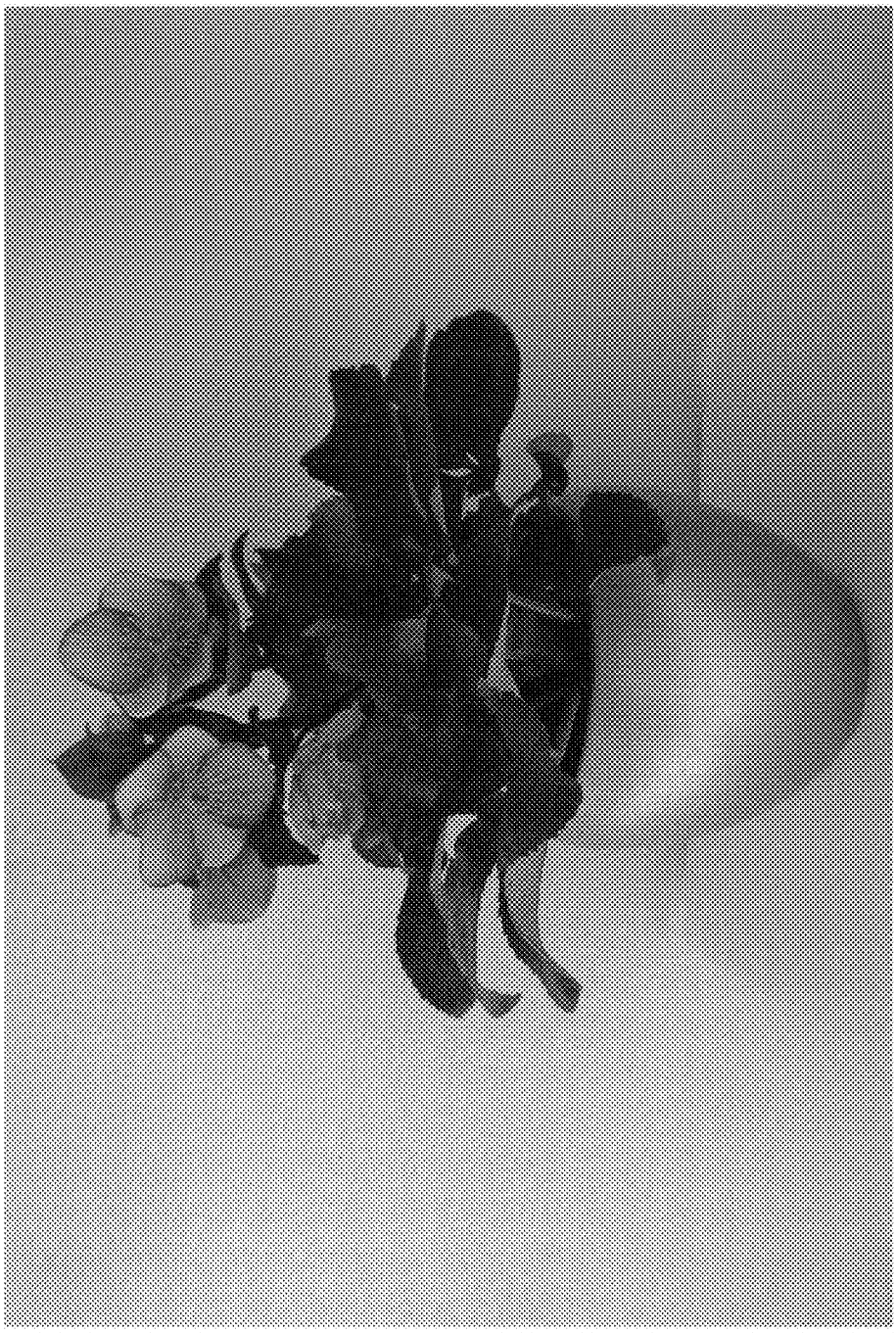

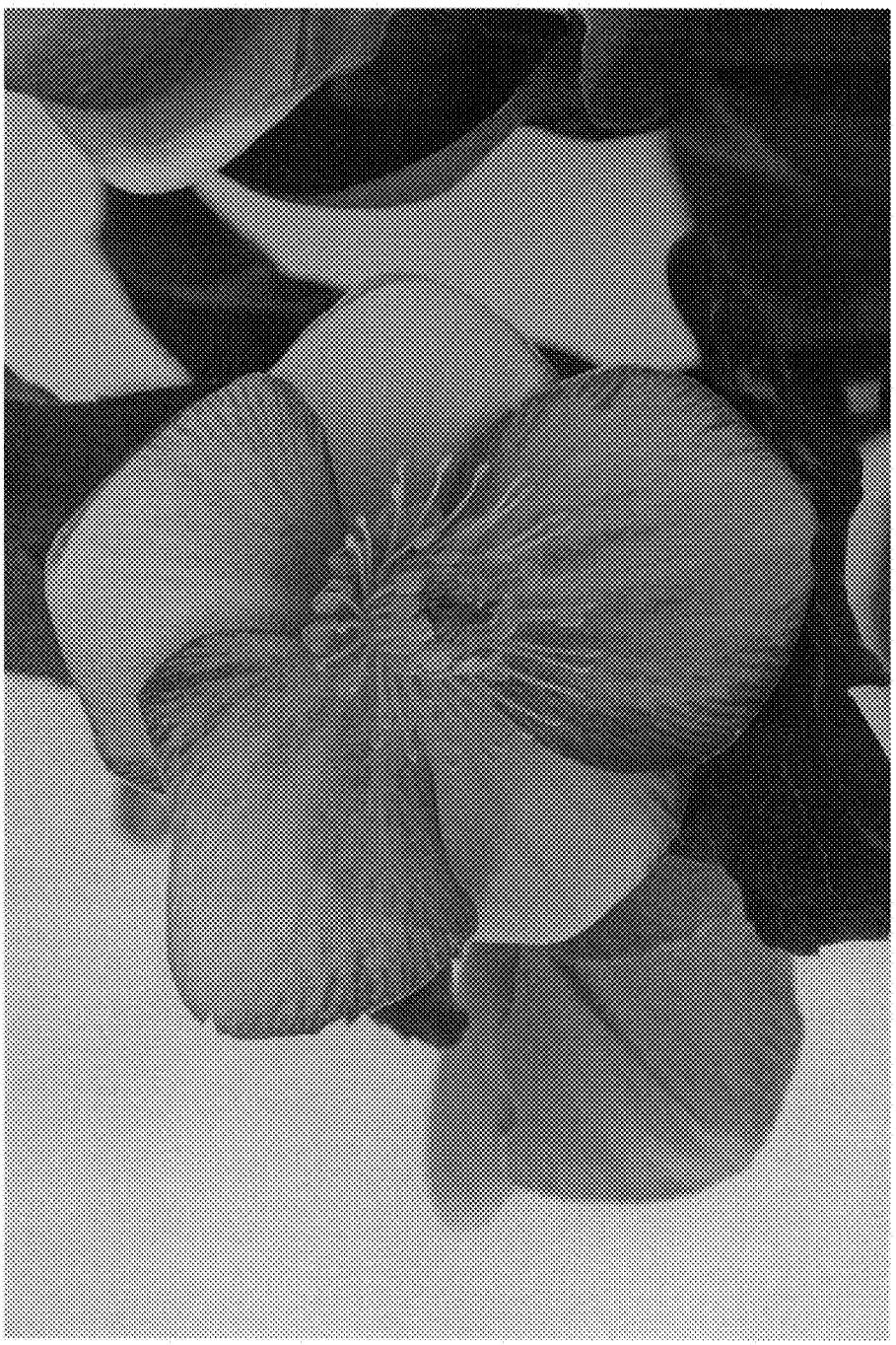

* * * * *